United States Patent
Sisler et al.

(10) Patent No.: US 10,670,541 B2
(45) Date of Patent: Jun. 2, 2020

(54) RADIO FREQUENCY BASED VOID FRACTION DETERMINATION

(71) Applicant: Steamfield Sensors, Inc., Scotts Valley, CA (US)

(72) Inventors: John R. Sisler, Scotts Valley, CA (US); Sadiq Jafar Mohammed Zarrouk, Auckland (NZ)

(73) Assignees: Steamfield Sensors, Inc., Scotts Valley, CA (US); Auckland UniServices Limited, Auckland (NZ)

( * ) Notice: Subject to any disclaimer, the term of this patent is extended or adjusted under 35 U.S.C. 154(b) by 339 days.

(21) Appl. No.: 15/667,442

(22) Filed: Aug. 2, 2017

(65) Prior Publication Data

US 2017/0328843 A1 Nov. 16, 2017

Related U.S. Application Data

(63) Continuation of application No. 15/492,276, filed on Apr. 20, 2017, now abandoned, which is a
(Continued)

(51) Int. Cl.
*G01N 22/00* (2006.01)
*G01N 25/60* (2006.01)
(Continued)

(52) U.S. Cl.
CPC ............. *G01N 22/00* (2013.01); *G01F 1/56* (2013.01); *G01F 1/586* (2013.01); *G01F 1/60* (2013.01);
(Continued)

(58) Field of Classification Search
CPC ... G01F 1/56; G01F 1/586; G01F 1/60; G01F 1/66; G01F 1/662; G01F 1/74;
(Continued)

(56) References Cited

U.S. PATENT DOCUMENTS 3,529,234 A 9/1970 Keen
5,103,181 A * 4/1992 Gaisford ............ G01N 33/2823
324/637

(Continued)

OTHER PUBLICATIONS

International Search Report and Written Opinion of the International Searching Authority dated Jan. 8, 2016, which issued during prosecution of International Application No. PCT/US2015/056251.

*Primary Examiner* — Wyatt A Stoffa
(74) *Attorney, Agent, or Firm* — Perkins Coie LLP; Brian Coleman

(57) ABSTRACT

Several embodiments include a method of computing void fraction in a two-phase mixture in a pipe. A driver and a transmitter antenna can transmit a radio frequency (RF) signal through the pipe. The pipe can convey the two-phase mixture extracted from a geothermal well. The RF signal can pass through the two-phase mixture. A receiver antenna in the pipe can receive the RF signal. A receiver circuit can measure signal strength attenuations of the RF signal at the receiver antenna over a time window. A computation engine can compute an average of the signal strength attenuations over the time window. The computation engine or another computing device can then compute, in real-time, a change in a void fraction of the two-phase mixture based on the average of the signal strength attenuations.

24 Claims, 4 Drawing Sheets

Related U.S. Application Data continuation of application No. PCT/US2015/056251, filed on Oct. 19, 2015.

(60) Provisional application No. 62/067,377, filed on Oct. 22, 2014.

(51) Int. Cl.

| | | |
|---|---|---|
| *G01F 1/56* | (2006.01) | |
| *G01F 1/58* | (2006.01) | |
| *G01F 1/60* | (2006.01) | |
| *G01F 1/74* | (2006.01) | |
| *G01N 33/24* | (2006.01) | |
| *H01Q 1/22* | (2006.01) | |
| *H01Q 1/44* | (2006.01) | |
| *G01N 27/02* | (2006.01) | |

(52) U.S. Cl.
CPC .............. *G01F 1/74* (2013.01); *G01N 25/60* (2013.01); *G01N 27/02* (2013.01); *G01N 33/24* (2013.01); *H01Q 1/2233* (2013.01); *H01Q 1/44* (2013.01)

(58) Field of Classification Search
CPC .... G01N 33/2823; G01N 25/60; G01N 22/00; G01N 27/02
See application file for complete search history.

(56) References Cited

U.S. PATENT DOCUMENTS

| | | | |
|---|---|---|---|
| 5,203,211 A * | 4/1993 | Jung | G01F 15/08 73/861.04 |
| 5,576,974 A * | 11/1996 | Marrelli | G01N 22/00 324/637 |
| 5,793,216 A * | 8/1998 | Constant | G01F 1/663 324/639 |
| 6,282,497 B1 | 8/2001 | Bharathan | |
| 6,831,470 B2 * | 12/2004 | Xie | G01N 27/06 324/693 |
| 7,640,133 B2 * | 12/2009 | Monmont | E21B 43/24 702/136 |
| 8,536,883 B2 * | 9/2013 | Xie | G01N 22/00 324/691 |
| 8,570,050 B2 * | 10/2013 | Nyfors | G01F 1/74 324/634 |
| 8,960,016 B2 * | 2/2015 | Wee | G01F 1/363 73/861.04 |
| 2003/0011386 A1 * | 1/2003 | Xie | G01N 22/00 324/694 |
| 2003/0056602 A1 * | 3/2003 | Cushing | G01F 1/60 73/861.17 |
| 2003/0074982 A1 * | 4/2003 | Spielman | G01F 1/74 73/861.63 |
| 2003/0136185 A1 * | 7/2003 | Dutton | E21B 43/36 73/61.44 |
| 2007/0027638 A1 * | 2/2007 | Fernald | G01F 1/712 702/25 |
| 2007/0044572 A1 * | 3/2007 | Davis | G01F 1/66 73/861.42 |
| 2009/0271129 A1 * | 10/2009 | Monmont | E21B 43/24 702/50 |
| 2011/0012626 A1 * | 1/2011 | Scott | G01N 33/2823 324/695 |
| 2011/0144947 A1 | 6/2011 | Myougan | |
| 2011/0196625 A1 * | 8/2011 | Sheila-Vadde | G01F 1/66 702/49 |
| 2011/0301877 A1 * | 12/2011 | Wee | G01F 1/363 702/47 |
| 2013/0327154 A1 * | 12/2013 | Xie | G01N 22/00 73/861.04 |
| 2014/0311251 A1 * | 10/2014 | Hutchinson | G01N 27/226 73/861.04 |
| 2015/0075629 A1 | 3/2015 | Davis | |
| 2015/0097579 A1 * | 4/2015 | Sharma | G01N 22/00 324/637 |
| 2015/0115979 A1 * | 4/2015 | Nyfors | G01N 33/2823 324/633 |
| 2016/0161425 A1 * | 6/2016 | Berezin | G01N 22/00 324/638 |
| 2016/0245684 A1 * | 8/2016 | Wee | G01F 1/74 |

* cited by examiner

RADIO FREQUENCY BASED VOID FRACTION DETERMINATION

CROSS REFERENCE TO RELATED APPLICATION(S)

This application is a continuation application of U.S. patent application Ser. No. 15/492,276, filed Apr. 20, 2017, which is a continuation application of International Application No. PCT/US2015/056251, filed Oct. 19, 2015, which claims the benefit of U.S. Provisional Patent Application No. 62/067,377, filed Oct. 22, 2014 all of which are incorporated herein in their entirety by reference.

RELATED FIELD

At least one embodiment of this disclosure relates generally to a geothermal system, and in particular to determining void fraction in a geothermal system.

BACKGROUND

Supply of energy resources across the globe is becoming scarce. Various alternative energy sources have been explored, including solar, wind, tidal, and geothermal. Because all of these alternative sources may be unpredictable, various systems have been implemented to accurately and consistently estimate and model the energy output and characteristics of these sources.

Geothermal energy is thermal energy generated and stored in the Earth. From hot springs or other thermal vents, geothermal energy can be extracted and converted into electrical energy. For geothermal, the measurement of void fraction from each geothermal well/vent/spring enables the operators of geothermal wells to calculate the total enthalpy of the two-phase fluids produced from the well, and hence, estimate the energy output. Void fraction or porosity is a measure of the void (i.e., "empty") spaces in a material, and a fraction of the volume of voids over the total volume. For example, the void fraction can be expressed as between 0 and 1 or as a percentage between 0 and 100%. A pump can extract both steam and water (e.g., brine) out of a geothermal vent, creating a gas-liquid two-phase flow. The void fraction can be defined as the fraction of the flow channel volume that is occupied by the gas phase (e.g., steam) or, alternatively, as the fraction of the cross-sectional area of the channel that is occupied by the gas phase.

Conventional techniques of measuring void fraction mostly involve taking the geothermal system out of commission temporarily. For example, a conventional method involves redirecting the output flow from a geothermal well into a separator/silencer assembly to measure the ratio of steam flow and water flow. For another example, the output flow may be redirected into a pressure-controlled pipe to estimate the void fraction. These techniques are disruptive to the energy production cycle of a geothermal power plant.

Recent developments led to a technique of measuring the void fraction via precise metered injection of liquid and vapor phase tracers into the two-phase production pipeline and sampling each phase downstream of the injection point. While this technique does not disrupt the production pipeline, this technique does require additional lab work and does not provide instantaneous feedback of the geothermal well's performance.

DISCLOSURE OVERVIEW

Some embodiments disclose techniques for estimating void fractions in real-time or substantially real-time without disrupting the production flow of the geothermal power plant. Some embodiments describe methods and systems of determining void fraction of a two-phase mixture extracted from a geothermal well by measuring the attenuations of one or more radiofrequency (RF) signals in a fixed span of a transportation unit (e.g., a pipe). Depending on void fraction of the two-phase mixture in the transportation, the RF signals would attenuate differently across the fixed span. For example, a monitor system can utilize one or more transmitter antennas in the transportation unit to transmit one or more RF signals and utilize one or more receiver antennas to measure attenuations of these RF signals over the fixed span. In some embodiments, an antenna can be configured to serve as both a transmitter antenna and a receiver antenna. For example, a chain of antennas can enable the monitor system to measure RF signal attenuation across multiple sequential spans of the transportation unit. In some embodiments, each antenna is configured to serve as either a transmitter antenna or a receiver antenna. For example, pairs of transmitter antenna and receiver antenna can be distributed within the transportation unit.

The void fraction changes when the ratio between liquid brine and geothermal vapor (e.g., steam and/or other gases) changes. When the ratio between the liquid brine and the geothermal vapor changes, the attenuation of the RF signals traversing through the two-phase mixture also changes (e.g., more liquid leads to higher attenuation). In some embodiments, the structure of antennas are adapted with aerodynamic and/or hydrodynamic designs (e.g., protected with a hydrodynamic and aerodynamic shield) to avoid breakage or damage from sudden movements of the two-phase mixture. In some embodiments, the antennas are secured onto the transformation unit with dampeners to prevent damages due to large oscillations or vibrations of the transportation unit. The attenuation values can be averaged (e.g., 5 minute intervals) to determine the void fraction of the mixture in real-time (e.g., by a moving average). In some embodiments, the signal attenuation can be computed logarithmically, such as in units of decibels.

Some embodiments of this disclosure have other aspects, elements, features, and steps in addition to or in place of what is described above. These potential additions and replacements are described throughout the rest of the specification

The figures depict various embodiments of this disclosure for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
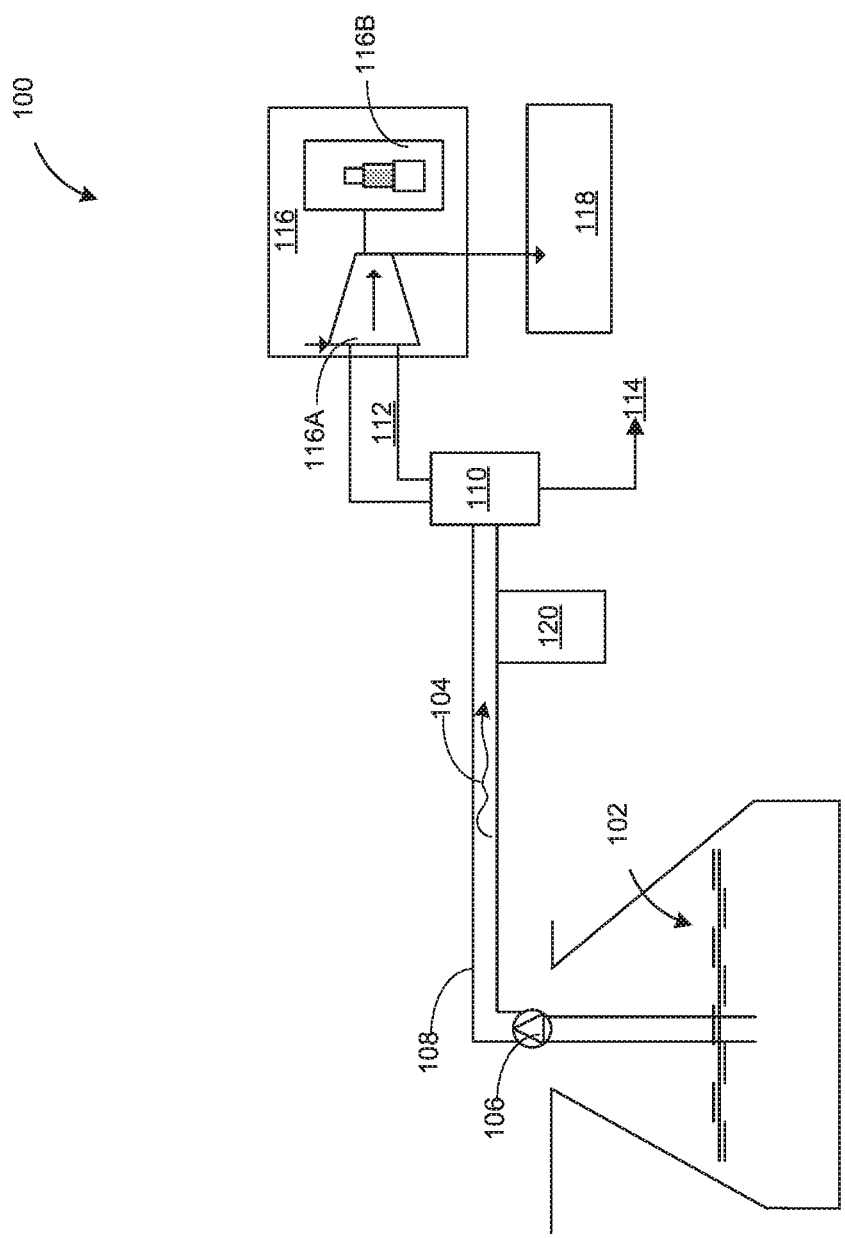
FIG. 1 is a diagram illustrating a geothermal power plant, in accordance with various embodiments.

FIG. 1 illustrates a geothermal power plant 100, in accordance with various embodiments. The geothermal power plant 100 comprises a geothermal well 102 producing a two-phase mixture 104, such as saturated steam and hot brine, taken via an extraction unit 106. The two-phase mixture 104 is then transported via a transportation unit 108 (e.g., a pipe) to a separator 110. In some embodiments, the separator 110 can be connected to multiple transportation units, such as the transportation unit 108, each conveying two-phase mixture from a different geothermal well, such as the geothermal well 102. The separator 110 can balance the pressure of the two-phase mixtures coming from all of the transportation units. The separator 110 separates geothermal vapor 112 (e.g., the saturated steam and non-condensable gases) from geothermal liquid 114. The separator 110 then supplies the geothermal vapor 112 to a generator unit 116.

The generator unit 116, for example, can be a turbogenerator including a turbine 116A driving an electric generator 116B. The generator unit 116 extracts heat (e.g., stored in enthalpy) from the steam and produces power, such as electrical power. In some embodiments, the heat-depleted steam exhausted from the generator unit 116 is condensed via a condenser 118 that is supplied with cooling water or other coolant. Water vapor and other non-condensable gases are vented to the atmosphere and hot brine produced from the separator 110 is collected and conveyed back to the geothermal well or to a storage area.

In various embodiments, the geothermal power plant 100 also includes a void fraction monitor 120. The void fraction monitor 120 can determine the void fraction of the two-phase mixture 104 without disrupting the operation of the generator pipeline. The void fraction monitor 120 can determine a real-time or substantially real-time void fraction of the two-phase mixture 104 in the transportation unit 108 by measuring attenuation of an RF signal traveling through the two-phase mixture 104 in the transportation unit 108. In some embodiments, the void fraction monitor 120 can measure attenuations of multiple RF signals (e.g., at different modulations or frequencies) traveling through the two-phase mixture 104. In some embodiments, the void fraction monitor 120 can measure attenuations of multiple RF signals traveling through the two-phase mixture 104 in different segments of the transportation unit 108. In some embodiments, the void fraction monitor 120 is implemented with at least an antenna for transmitting an RF signal, an antenna for receiving the RF signal, control circuitry to modulate/transmit the RF signal, control circuitry to receive/measure the RF signal, and a computer system to compute the void fraction based on the attenuation of the RF signal.

Figure 2:
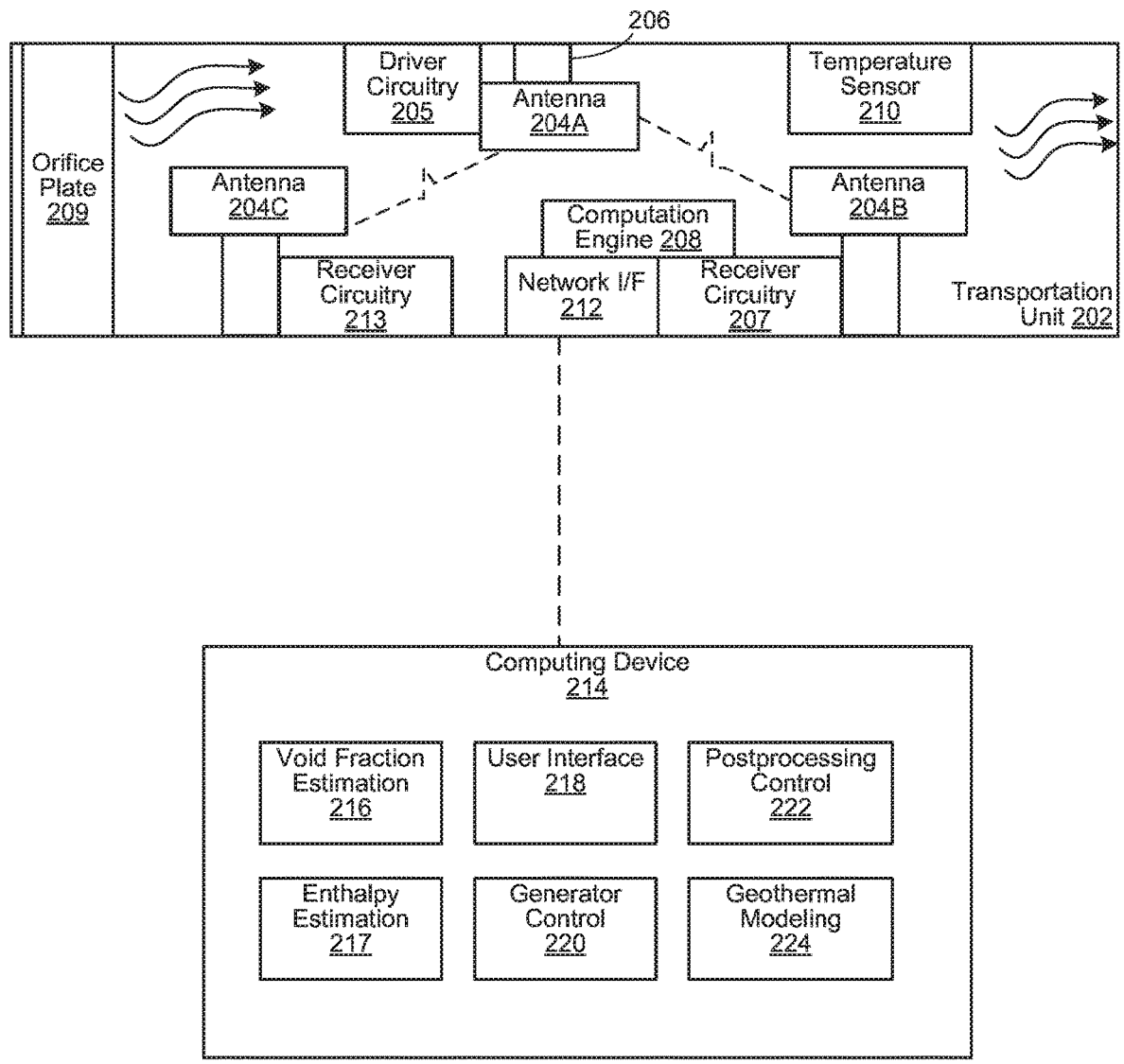
FIG. 2 is a block diagram illustrating a void fraction monitor, in accordance with various embodiments.

FIG. 2 is a block diagram illustrating a void fraction monitor 200, in accordance with various embodiments. The void fraction monitor 200, for example, can be the void fraction monitor 120 of FIG. 1. The void fraction monitor 200 can be coupled to a transportation unit 202, such as the transportation unit 108 of FIG. 1. The void fraction monitor 200 includes one or more antennas 204 (e.g., a transmitter antenna 204A, a receiver antenna 204B, and optionally a receiver antenna 204C). The receiver antenna 204B can be downstream from the transmitter antenna 204A and the receiver antenna 204C can be upstream from the transmitter antenna 204A. For example, the receiver antenna 204C can be at a first distance away from the transmitter antenna 204A different from a second distance between the transmitter antenna 204A and the receiver antenna 204B.

The antennas 204 may be secured onto an inner side of the transportation unit 202 via an attachment mechanism 206. The attachment mechanism 206, for example, can be a fastener, a clip, or a joint. The attachment mechanism 206 can also include a dampening structure to protect the antennas 204 from overstressing or being damaged by vibrations of the transportation unit 202 or oscillations (e.g., by slug flow) of the two-phase mixture in the transportation unit 202. The antennas 204 can be adapted with a hydrodynamic or aerodynamic shield that prevents it from being damaged by slug flow.

A driver circuitry 205 can power the transmitter antenna 204A to send an RF signal towards the receiver antenna 204B and the receiver antenna 204C. In some embodiments, the RF signal is a directional RF signal. In some embodiments, the RF signal is an omni-directional RF signal. In various embodiments, measuring the attenuation of an RF signal is advantageous over measuring attenuation of a light beam. A light beam requires a line of sight, and hence the alignment of a light emitter and an optical sensor need to be precise. The RF signal on the other hand can bounce multiple times on an inner surface of the transportation unit 202, and still be captured by a receiver antenna. While an optical sensor can be blinded or covered by debris, a receiver antenna generally do not get blinded by debris.

In some embodiments, RF signal is within the microwave frequency range (e.g., 300 MHz to 300 GHz). In some embodiments, the driver circuitry 205 includes an amplifier and/or a modulator. The driver circuitry 205 can have its own power source, or receive power (AC or DC) from a power supply outside of the transportation unit 202.

In a particular example, the driver circuitry 205 includes a noise source (e.g., a diode driven in reverse to generate a broadband white noise) coupled to a microwave amplifier. In some embodiments, the driver circuitry 205 can use a modulator instead or in addition to the noise source. The modulator may be capable of generating specific signal patterns at specific frequencies. The microwave amplifier can be coupled to a circulator. Because of the changes in the void fraction that the transmitter antenna 204A is immersed in, the impedance at the transmitter antenna 204A can vary drastically. The circulator can act as a duplexer/isolator to re-route any reverse signal that bounces back from transmitter antenna 204A. For example, a reverse signal may fry the microwave amplifier without the presence of the circulator. The circulator is coupled to the microwave amplifier at a first port and to the transmitter antenna 204A at a second port. The circulator re-routes the reverse signal to a third port. The driver circuitry 205 can measure the reverse/reflected signal strength to determine how much of transmitted power has been reflected back. The void fraction monitor 200 can thus determine the attenuation through the two-phase mixture by subtracting the inputting power by both the received power at the receiver antenna 204B and the reverse signal power at the transmitter antenna 204A. The same process can be made between the receiver antenna 204C and the transmitter antenna 204A.

A receiver circuitry 207 can be coupled to the receiver antenna 204B to interpret the RF signal received by the receiver antenna 204B. The same receiver circuitry 207 can be coupled to the receiver antenna 204C. In some embodiments, the receiver antenna 204C can have its own receiver circuitry 213. Because the attenuation of the RF signal traveling through the two-phase mixture in the transportation unit 202 may be high, the receiver circuitry 207 can include a pre-amp before measuring the RF signal. In some embodiments, the receiver circuitry 207 can include a RF power meter (e.g., a diode and a capacitor) to measure the received power regardless of the frequency. In some embodiments, the receiver circuitry 207 can include a receiver, a filter, a demodulator, a detector, a software-defined radio (SDR), a spectrum analyzer, or any combination thereof, to determine the attenuation of the RF signal at one or more preset frequencies. In the embodiments where the receiver circuitry 207 can measure attenuation levels at different frequencies, the receiver circuitry 207 can share those additional information with a computing system of the void fraction monitor 200 to derive additional information about the two-phase mixture other than void fraction (e.g., carbon dioxide content or other content). The void fraction monitor can then determine the void fraction associated with the levels of attenuation at the preset frequencies. For example, 3 dB of attenuation at a 1.5 GHz frequency can correspond to approximately 2% change in void fraction.

In some embodiments, the receiver circuitry 207 can be coupled to a computation engine 208. The receiver circuitry 213 can also be coupled to the computation engine 208. The computation engine 208 can be implemented by the receiver circuitry 207, by a separate circuit, or by a computing device. The computation engine 208, for example, can compute and an attenuation reading based on a receiver antenna signal strength observed by the receiver circuitry 207 and a known transmission signal strength. The known transmission signal strength can be provided by the driver circuitry 205 or preprogrammed into the receiver circuitry 207 or the computation engine 208.

In some embodiments, the transportation unit 202 includes an orifice plate 209 therein that measures velocity of flow and/or pressure of the mixture in the transportation unit. In some embodiments, the transportation unit 202 includes a temperature sensor 210 therein that measures the temperature of the mixture. In some embodiments, the transportation unit 202 includes a network interface 212 (e.g., a wireless transceiver or a wired transceiver). The network interface 212 can be coupled to the receiver circuitry 207 and/or the receiver circuitry 213. The network interface 212 can transmit the pressure measurement, the temperature measurement, the attenuation measurements, or any combination thereof, to a computing system 214 (e.g., one or more computing devices). In some embodiments, the computing system 214 is located within the transportation unit 202. In some embodiments, the computing system 214 is located outside of the transportation unit 202. In some embodiments, the computing system 214 can be directly coupled via one or more wires/cables to the orifice plate 209, the temperature sensor 210, the receiver circuitry 207 (e.g., reporting the received signal power or the attenuation), the driver circuitry 205 (e.g., reporting the inputting signal strength and/or the reflected/reverse signal strength), or any combination thereof.

The computing system 214 can compute the void fraction using the changes in average attenuation at one or more frequencies (or average of changes in the attenuation) as measured at the receiver circuitry 207. The computing system 214 can then compute the total heat content (e.g., enthalpy) extracted from the geothermal well through the transportation unit 202 based on the pressure measurement, the temperature measurement, and the void fraction estimation.

The computing system 214 can be implemented by one or more computing devices, such as a single processor or multi-processor computer, a distributed computing cluster, a virtualized operating system hosted by a cloud server farm, etc. The computing system 214 can implement one or more functional modules (e.g., as software component or hardware component in the computing system 214). For example, the computing system 214 can include a void fraction estimation module 216, an enthalpy estimation module 217, a user interface module 218, a generator control module 220, a post-processing control module 222, and a geothermal modeling module 224. One or more of these modules can be implemented in the computation engine 208, the receiver circuitry 207, and/or the computing system 214.

The void fraction estimation module 216 can receive the attenuation measurements from the receiver circuitry 207. The void fraction estimation module 216 can use the attenuation values to compute the void fraction of the two-phase mixture in the transportation unit 202 in substantially real-time. The void fraction estimation module 216 can also normalize out noise patterns in the attenuation measurements attributed to various phenomenon of a two-phase mixture flow. For example, the void fraction estimation module 216 can estimate the void fraction via differences between moving averages or periodic averages of attenuation measurements. Alternatively, the void fraction estimation module 216 can estimate the void fraction via averages of the differences between attenuation measurements.

The void fraction estimation module 216 can implement "virtual dampeners" that analyzes the chaotic signal being obtained from the antennas 204 and normalize out any static signal to get a clearer estimation of the void fraction. When the static signal is discounted, the average attenuation of the transportation unit and content inside can be monitored to estimate the void fraction of the content.

Based on the void fraction estimation, velocity flow/pressure information, and/or temperature information, the enthalpy estimation module 217 can dynamically compute enthalpy in the content of the transportation unit 202 in real-time. This enthalpy estimation can be presented via the user interface module 218. The user interface module 218 can present information about the geothermal well on a display device, via webpage, via an application programming interface (API), an audio speaker, or any combination thereof.

In some embodiments, the estimated enthalpy can be used to control the generator at the geothermal power plant via the generator control module 220, such as controlling a valve to the turbine coupled to the generator. In some embodiments, the estimated enthalpy and the estimated void fraction can be used to control the postprocessing of the geothermal content (e.g., steam and brine) via the postprocessing control module 222. For example, decreasing enthalpy can indicate breakthrough of injection water or invasion of cooler groundwater. Hence, upon detecting decreasing enthalpy, the postprocessing control module 222 can temporarily stop or decrease the injection of water down the geothermal well. For another example, increasing enthalpy can indicate reservoir boiling and the formation of a steam cap. In some cases, enthalpy is essential for the interpretation of geochemical data because it determines the steam fraction at sampling conditions and allows the correction of chemical concentrations back to reservoir conditions The geothermal modeling module 224 can use the real-time sensor data from the temperature sensor 210, the receiver circuitry 207, and the orifice plate 209 to determine context information about the heat production from the geothermal well. In some cases, the geothermal modeling module 224 can determine potential failure points in the geothermal power plant. For example, a first pattern of noisy variations in attenuation measurements may trigger an alert that a valve is chattering and about to fail. For another example, a second pattern of noisy variations in attenuation measurements may trigger an alert of the occurrence of slug flow. Unlike convention geothermal reservoir models that are static in nature, the geothermal modeling module 224 can maintain a real-time, dynamic model of a geothermal reservoir (e.g., multiple geothermal wells) based on the real-time enthalpy content (e.g., computed from the void fraction) produced from the geothermal wells of the geothermal reservoir.

The geothermal modeling module 224 can alert a user through the user interface module 218 when a slug flow pattern is determined. Slug flow pattern prediction can be achieved by monitoring the flow velocity with the orifice plate 209 and/or estimation of the void fraction. The combined information from the orifice plate 209 and the dynamic estimation of void fraction enables the geothermal modeling module 224 to detect onset triggers of slug flow and/or cyclical patterns of slug flow. This is advantageous over traditional systems that lack the ability to dynamically estimate void fraction during production. These contextual patterns, including slug flow patterns, can be time-stamped and tagged with other metadata (e.g., location, magnitude, frequency, etc.) such that the onset of these patterns (e.g., slug flow) can be compared with other phenomenon being measured around the steam field of the geothermal well or geothermal wells of the same reservoir.

In some embodiments, the geothermal modeling module 224 can be used to model the reservoir underneath the geothermal well by combining data from multiple geothermal wells connecting to the same reservoir. Traditionally, because void fraction cannot be tracked in real-time, modeling of a reservoir is accomplished by building a static reservoir model to balance the extraction of the two-phase mixture from different geothermal wells and re-injection of the water/liquid back to the geothermal wells. In some embodiments, the geothermal modeling module 224 can generate a 3D map of the reservoir based on the locations of the geothermal wells. The 3D map can illustrate a heat map corresponding to the enthalpy computed by the computing system 214 in real-time. With multiple geothermal wells monitored, and all the results aggregated in a 3D spatial model/display, for example, the geothermal modeling module 224 can accurate predict trigger-based and cyclical behaviors of a geothermal well or reservoir. The triggers and cycles of these behaviors can be identified using statistical analysis (e.g., principal component analysis and/or regression), signal analysis (e.g., Fourier transform and/or autocorrelation) and/or machine learning (e.g., Hidden Markov Model or Gaussian Mixture Model).

In several embodiments, the antennas 204, the driver circuitry 205, the receiver circuitry 207, the computation engine 208, or any combination thereof, are attached inside a pipe (e.g., the transportation unit 202 and/or the transportation unit 108). In several embodiments, at least one of the driver circuitry 205, the receiver circuitry 207, or the computation engine 208 is external to the pipe. In some embodiments, the computing system is attached inside the pipe as well. In other embodiments, the computing system is attached outside of the pipe.

Portions of active components (e.g., sensors, computing devices, functional modules, etc.) associated with the void fraction monitor 200 may be implemented in the form of special-purpose circuitry, in the form of one or more appropriately programmed programmable processors, a single board chip, a field programmable gate array, a network capable computing device, a virtual machine, a cloud-based terminal, or any combination thereof. For example, the components described can be implemented as instructions on a tangible storage memory capable of being executed by a processor or other integrated circuit chip. The tangible storage memory may be volatile or non-volatile memory. In some embodiments, the volatile memory may be considered "non-transitory" in the sense that it is not transitory signal. Memory space and storages described in the figures can be implemented with the tangible storage memory as well, including volatile or non-volatile memory.

Each of the components may operate individually and independently of other components. Some or all of the components may be executed on the same host device or on separate devices. The separate devices can be coupled through one or more communication channels (e.g., wireless or wired channel) to coordinate their operations. Some or all of the components may be combined as one component. A single component may be divided into sub-components, each sub-component performing separate method step or method steps of the single component.

In some embodiments, at least some of the components share access to a memory space. For example, one component may access data accessed by or transformed by another component. The components may be considered "coupled" to one another if they share a physical connection or a virtual connection, directly or indirectly, allowing data accessed or modified from one component to be accessed in another component. In some embodiments, at least some of the components can be upgraded or modified remotely (e.g., by reconfiguring executable instructions that implements a portion of the components). The void fraction monitor 200 may include additional, fewer, or different components for various applications.

Figure 3:
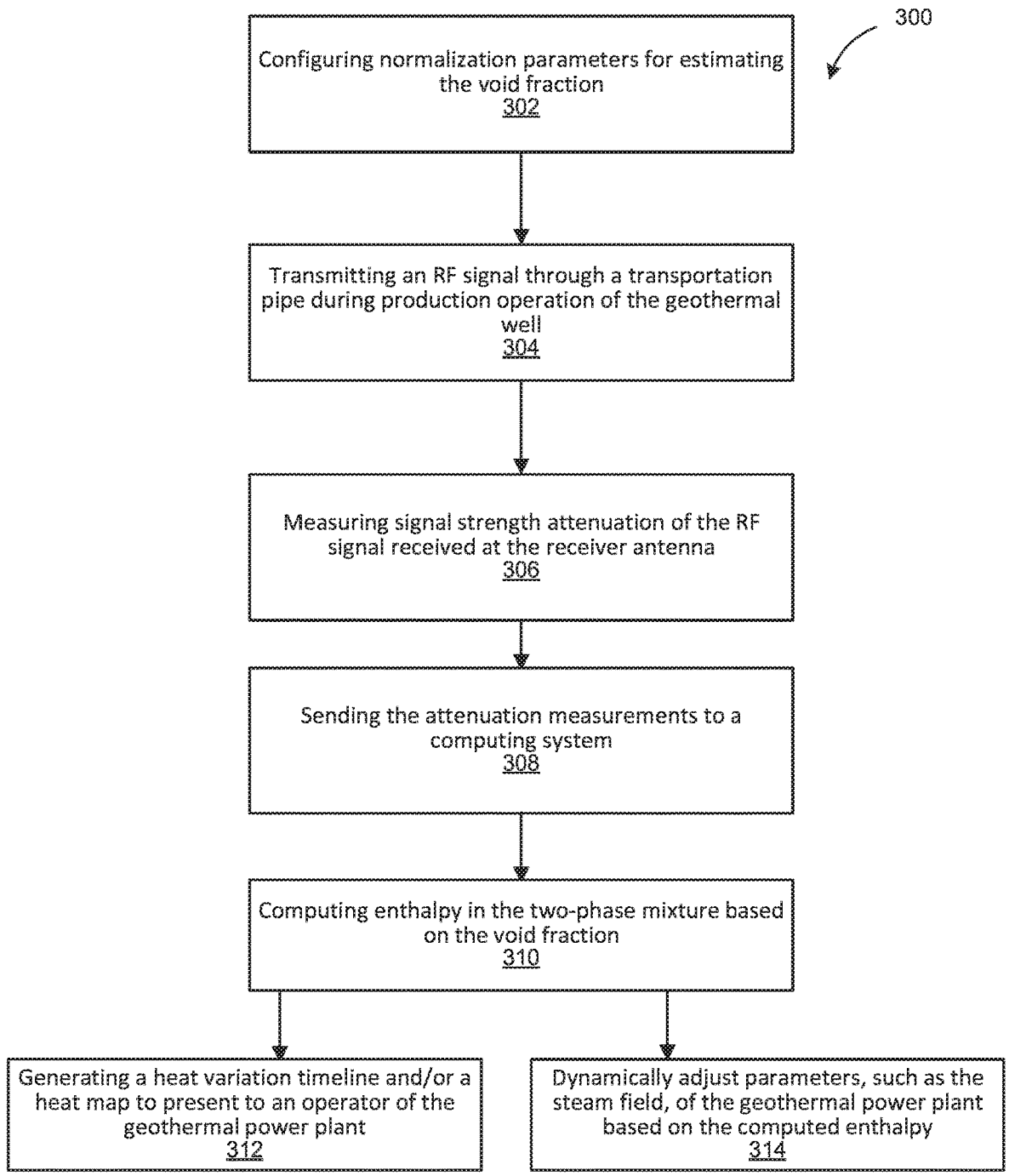
FIG. 3 is a flow chart of a method of operating a void fraction monitor at a geothermal power plant, in accordance with various embodiments.

FIG. 3 is a flow chart of a method 300 of operating a void fraction monitor (e.g., the void fraction monitor 200 of FIG. 2) at a geothermal power plant, in accordance with various embodiments. The method 300 begins at step 302 of configuring normalization parameters for estimating the void fraction. For example, the normalization parameters can include the levels of RF signal strength that a transmitter circuitry used. The normalization parameters can include an expected signal attenuation pattern (e.g., a spectral analysis pattern) when the two-phase mixture is completely vapor, when the two-phase mixture is completely liquid, and/or when the transportation pipe is empty.

In some embodiments, a computing system (e.g., the computing device 400 of FIG. 4) of the void fraction monitor can present an interface (e.g., a display and keyboard or a touchscreen) for a user to input the normalization parameters. In some embodiments, the normalization parameters can be estimated based on contextual information. For example, the user can input the length and thickness of the transportation pipe, and the computing system can estimate the attenuation pattern based on that information. The computing system can also estimate an expected signal strength variance due to noise rather than changes in void fraction.

In some embodiments, the computing system can calibrate the void fraction estimation algorithm prior to production operation of a geothermal well. For example, the computing system can instruct the transmitter circuit transmit when a transportation pipe is empty, when the transportation pipe is full of vapor, or when the transportation pipe is full of liquid. The computing system can collect the received signal strength (e.g., from the receiver circuit), the inputting signal strength (e.g., from the transmitter circuit), and the reflected/reverse signal strength (e.g., from the transmitter circuit) to determine the expected attenuation patterns at the upper and lower void fraction limits.

At step 304, a transmitter circuit can transmit an RF signal through a transportation pipe during production operation of the geothermal well. The transportation pipe may be conveying a two-phase mixture extracted from the geothermal well when the RF signal is transmitted. The RF signal propagates through the two-phase mixture. In turn, the two-phase mixture attenuates the signal strength of the RF signal. The two-phase mixture can have one or more material substances in at least two of solid phase, liquid phase, and gaseous phase.

A receiver antenna then captures the RF signal at a fixed distance away from the transmitter antenna. At step 306, a receiver circuit measures signal strength attenuation of the RF signal received at the receiver antenna. For example, the receiver circuit can measure signal strength attenuations of the RF signal at the receiver antenna over a time window. The receiver circuit can measure the signal strength attenuations logarithmically. A computation engine (e.g., the receiver circuit, a computing device, or another circuit) can compute an average of the signal strength attenuations over the time window. For example, the time window is a sliding time window and the average is a moving average.

In order to optimize the steam field to achieve an optimal efficiency, the void fraction monitor has to discern changes in the void fraction of the two-phase mixture within a certain resolution. Because the resolution of the void fraction estimation corresponds directly to signal attenuation measured at the receiver circuit, the initial signal strength modulated by the transmitter circuit can be increased when the receiver circuit is unable to detect the RF signal, such as when the signal attenuation is too high. Alternatively, a preamp at the receiver circuit can be selectively activated when the signal attenuation is too high. By selectively raising the initial signal strength and/or selectively using the preamp, the resolution of attenuation readings can be adjusted to match the resolution needed for estimating void fraction.

In some embodiments, steps 304 and 306 are repeated iteratively. To ensure that the power of the RF signal does not fry the circuitry used, the transmitter circuit can employ a feedback mechanism to determine the power used to modulate the RF signal. In some embodiments, the receiver circuit can communicate with the transmitter circuit. For example, the receiver circuit can communicate with the transmitter circuit via a cable or wirelessly. This enables the receiver circuit to provide feedback to the transmitter circuit. When the signal attenuation is too high (e.g., above a threshold), the transmitter circuit can then increase the initial signal strength to modulate the RF signal. When the received signal strength is too high (e.g., above a threshold) at the receiver antenna, the transmitter circuit can then decrease the initial signal strength when modulating the RF signal.

In some embodiments, the feedback mechanism can be a sensor (e.g., optical sensor, a temperature sensor, humidity sensor, or pressure sensor) that estimates, at a low resolution (e.g., lower than what the void fraction monitor can estimate), the void fraction of the two-phase mixture. This feedback mechanism enables the transmitter circuit to increase the power when the two-phase mixture has more liquid than vapor and decrease the power when the two-phase mixture has more vapor than liquid.

At step 308, the receiver circuit sends the attenuation measurements to the computing system. Based on at least the attenuation measurements, the known distance between the transmitter antenna and the receiver antenna, and/or the normalization parameters, the computing system can compute estimate a void fraction and/or a change in the void fraction of the two-phase mixture. The void fraction or the change of the void fraction can be specifically for a fixed span of the transportation pipe between a receiver antenna and a transmitter antenna that transmitted the RF signal. In some embodiments, the computing system can first compute the change in the void fraction, and then compute the void fraction based on the change in the void fraction and a stored calibration parameter. The calibration parameter can be associated with an average signal attenuation level. The calibration parameter can associate one or more signal attenuation levels at a given RF transmission setting (e.g., according to which the RF signal is generated) with one or more void fraction values. In these embodiments, the computing system can compute the void fraction by comparing the signal strength attenuation with the void fraction values with associated signal attenuation levels. The void fraction can be computed using a machine learning model or a statistical model that correlates potential signal strength attenuation levels to potential void fraction values.

In some embodiments, the computing system can estimate the void fraction based on a moving average of the attenuation measurements. The computing device can compute, in real-time, a change in a void fraction of the two-phase mixture based on the average of the signal strength attenuations. In some embodiments, one or more circuits can measure, simultaneously, signal strength attenuations of RF signals between multiple receiver/transmitter antenna pairs in sequential spans of the transportation pipe. Then the computing device can compute, in real-time, changes to void fractions of the two-phase mixture based on the signal strength attenuations of the RF signals between the multiple receiver/transmitter antenna pairs. A receiver antenna in one of the receiver/transmitter antenna pairs is a transmitter antenna in a subsequent one of the receiver/transmitter antenna pairs.

At step 310, the computing system can compute enthalpy in the two-phase mixture based on the void fraction or change to the void fraction. At step 312, the computing system can generate a heat variation timeline and/or a heat map to present to an operator of the geothermal power plant. The computing system can provide providing the enthalpy of the two-phase mixture to a monitor station external to the transportation pipe in real-time without disturbing or changing flow of the two-phase mixture. At step 314, the computing system can dynamically adjust parameters, such as the steam field, of the geothermal power plant based on the computed enthalpy.

While processes or methods are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. In addition, while processes or blocks are at times shown as being performed in series, these processes or blocks may instead be performed in parallel, or may be performed at different times.

Figure 4:
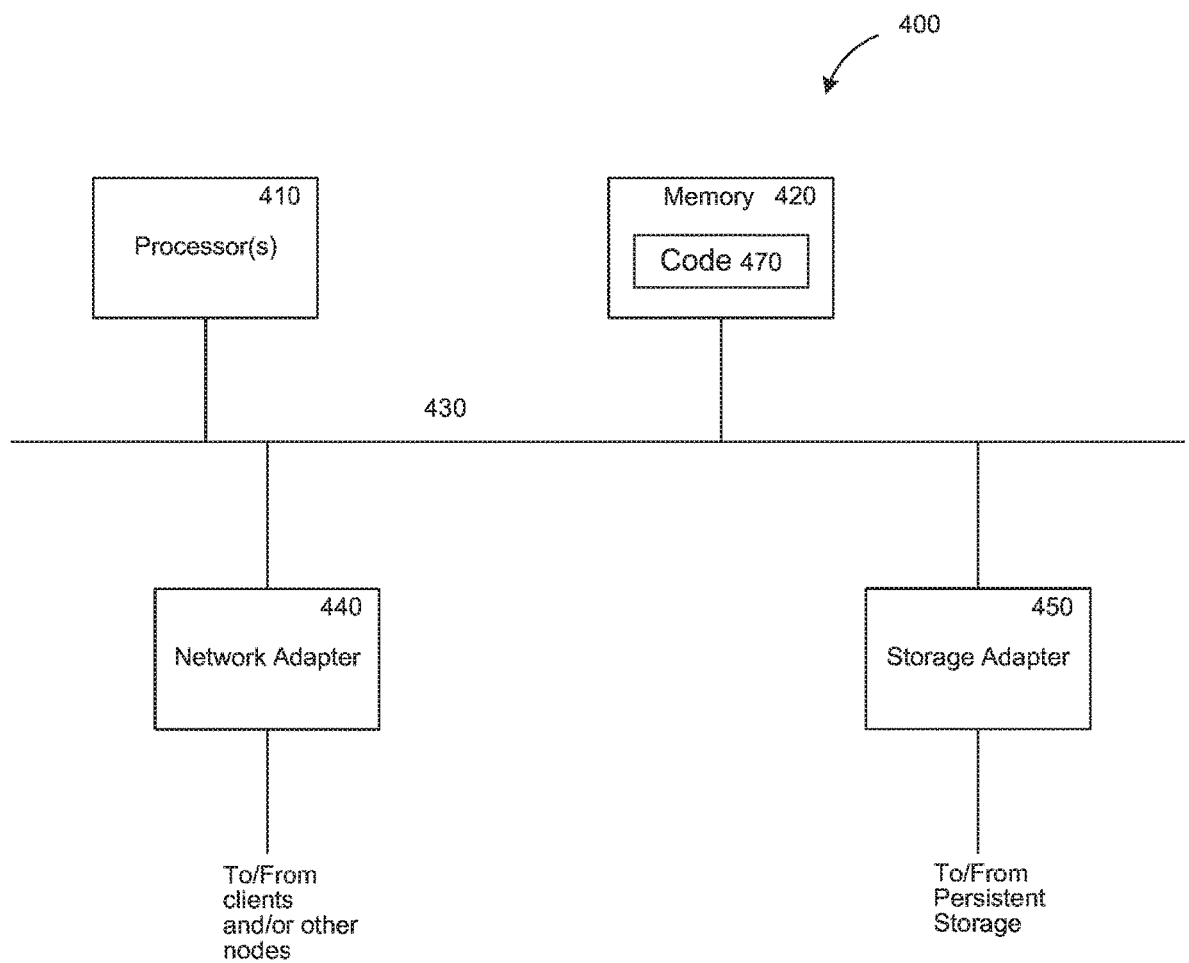
FIG. 4 is a block diagram of an example of a computing device, which may represent one or more computing device or server described herein, in accordance with various embodiments.

FIG. 4 is a block diagram of an example of a computing device 400, which may represent one or more computing device or server described herein, in accordance with various embodiments. The computing device 400 can be one or more computing devices that implement the void fraction monitor 200 of FIG. 2 or methods and processes described in this disclosure. The computing device 400 includes one or more processors 410 and memory 420 coupled to an interconnect 430. The interconnect 430 shown in FIG. 4 is an abstraction that represents any one or more separate physical buses, point-to-point connections, or both connected by appropriate bridges, adapters, or controllers. The interconnect 430, therefore, may include, for example, a system bus, a Peripheral Component Interconnect (PCI) bus or PCI- Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1494 bus, also called "Firewire".

The processor(s) 410 is/are the central processing unit (CPU) of the computing device 400 and thus controls the overall operation of the computing device 400. In certain embodiments, the processor(s) 410 accomplishes this by executing software or firmware stored in memory 420. The processor(s) 410 may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices.

The memory 420 is or includes the main memory of the computing device 400. The memory 420 represents any form of random access memory (RAM), read-only memory (ROM), flash memory, or the like, or a combination of such devices. In use, the memory 420 may contain a code 470 containing instructions according to the mesh connection system disclosed herein.

Also connected to the processor(s) 410 through the interconnect 430 are a network adapter 440 and a storage adapter 450. The network adapter 440 provides the computing device 400 with the ability to communicate with remote devices, over a network and may be, for example, an Ethernet adapter or Fibre Channel adapter. The network adapter 440 may also provide the computing device 400 with the ability to communicate with other computers. The storage adapter 450 enables the computing device 400 to access a persistent storage, and may be, for example, a Fibre Channel adapter or SCSI adapter.

The code 470 stored in memory 420 may be implemented as software and/or firmware to program the processor(s) 410 to carry out actions described above. In certain embodiments, such software or firmware may be initially provided to the computing device 400 by downloading it from a remote system through the computing device 400 (e.g., via network adapter 440).

The techniques introduced herein can be implemented by, for example, programmable circuitry (e.g., one or more microprocessors) programmed with software and/or firmware, or entirely in special-purpose hardwired circuitry, or in a combination of such forms. Special-purpose hardwired circuitry may be in the form of, for example, one or more application-specific integrated circuits (ASICs), programmable logic devices (PLDs), field-programmable gate arrays (FPGAs), etc.

Software or firmware for use in implementing the techniques introduced here may be stored on a machine-readable storage medium and may be executed by one or more general-purpose or special-purpose programmable microprocessors. A "machine-readable storage medium," as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible storage medium includes recordable/non-recordable media (e.g., read-only memory (ROM); random access memory (RAM); magnetic disk storage media; optical storage media; flash memory devices; etc.), etc.

The term "logic," as used herein, can include, for example, programmable circuitry programmed with specific software and/or firmware, special-purpose hardwired circuitry, or a combination thereof.

Some embodiments of the disclosure have other aspects, elements, features, and steps in addition to or in place of what is described above. These potential additions and replacements are described throughout the rest of the specification.

What is claimed is:

1. A method of computing void fraction in a two-phase mixture extracted at a geothermal power plant, comprising
    transmitting a radio frequency (RF) signal through a transportation pipe during production operation of a geothermal well, the transportation pipe conveying the two-phase mixture extracted from the geothermal well, wherein the RF signal passes through the two-phase mixture, wherein the two-phase mixture has one or more material substances in at least two of solid phase, liquid phase, and gaseous phase;
    receiving the RF signal at a receiver antenna in the transportation pipe;
    measuring signal strength attenuations of the RF signal at the receiver antenna over a time window;
    computing an average of the signal strength attenuations over the time window;
    computing, in real-time, a change in a void fraction of the two-phase mixture based on the average of the signal strength attenuations; and
    computing the void fraction using a machine learning model or a statistical model that correlates potential signal strength attenuation levels to potential void fraction values.

2. The method of claim 1, wherein the signal strength attenuations are measured logarithmically.

3. The method of claim 1, wherein the time window is a sliding time window and the average is a moving average.

4. The method of claim 1, further comprising, computing enthalpy in the two-phase mixture based on the change in the void fraction.

5. The method of claim 4, further comprising, providing the enthalpy of the two-phase mixture to a monitor station external to the transportation pipe in real-time without disturbing or changing flow of the two-phase mixture.

6. The method of claim 4, further comprising, dynamically adjusting geothermal wells of a same reservoir of the geothermal power plant based on the computed enthalpy.

7. The method of claim 1, further comprising, computing the void fraction based on the change in the void fraction and a calibration parameter associated with an average signal attenuation level.

8. The method of claim 1, wherein said transmitting is in accordance with a given RF transmission setting; and the method further comprising:
    storing a calibration parameter associating one or more signal attenuation levels at a given RF transmission setting with one or more void fraction values; and
    computing the void fraction by comparing the signal strength attenuation with the void fraction values with associated signal attenuation levels.

9. The method of claim 1, wherein the RF signal transmitted through the transportation pipe is multiple RF signals at different modulations or frequencies.

10. The method of claim 1, further comprising:
    detecting a pattern of noisy variations based on the signal strength attenuations; and
    sending an alert message based on the detecting of the pattern of noisy variations.

11. The method of claim 1, wherein the receiver antenna is adapted to transmit a signal, and wherein the RF signal transmitted through the transportation pipe is transmitted by the receiver antenna.

12. The method of claim 1, further comprising: measuring, simultaneously, signal strength attenuations of RF signals between multiple receiver/transmitter antenna pairs in sequential spans of the transportation pipe; and computing, in real-time, changes to void fractions of the two-phase mixture based on the signal strength attenuations of the RF signals between the multiple receiver/transmitter antenna pairs.

13. The method of claim 12, wherein a receiver antenna in one of the receiver/transmitter antenna pairs is a transmitter antenna in a subsequent one of the receiver/transmitter antenna pairs.

14. The method of claim 1, wherein computing the change of the void fraction is specifically for a fixed span of the transportation pipe between the receiver antenna and a transmitter antenna that transmitted the RF signal.

15. A method of computing void fraction in a two-phase mixture extracted at a geothermal power plant, comprising
transmitting a radio frequency (RF) signal through a transportation pipe during production operation of a geothermal well, the transportation pipe conveying the two-phase mixture extracted from the geothermal well, wherein the RF signal passes through the two-phase mixture, wherein the two-phase mixture has one or more material substances in at least two of solid phase, liquid phase, and gaseous phase;
receiving the RF signal at a receiver antenna in the transportation pipe;
measuring signal strength attenuations of the RF signal at the receiver antenna over a time window;
computing an average of the signal strength attenuations over the time window;
computing, in real-time, a change in a void fraction of the two-phase mixture based on the average of the signal strength attenuations;
detecting a pattern of noisy variations based on the signal strength attenuations; and
sending an alert message based on the detecting of the pattern of noisy variations.

16. The method of claim 15, wherein the signal strength attenuations are measured logarithmically.

17. The method of claim 15, wherein the time window is a sliding time window and the average is a moving average.

18. The method of claim 15, further comprising, computing enthalpy in the two-phase mixture based on the change in the void fraction.

19. The method of claim 18, further comprising, providing the enthalpy of the two-phase mixture to a monitor station external to the transportation pipe in real-time without disturbing or changing flow of the two-phase mixture.

20. The method of claim 18, further comprising, dynamically adjusting geothermal wells of a same reservoir of the geothermal power plant based on the computed enthalpy.

21. The method of claim 15, further comprising, computing the void fraction based on the change in the void fraction and a calibration parameter associated with an average signal attenuation level.

22. The method of claim 15, wherein said transmitting is in accordance with a given RF transmission setting; and the method further comprising:
storing a calibration parameter associating one or more signal attenuation levels at a given RF transmission setting with one or more void fraction values; and
computing the void fraction by comparing the signal strength attenuation with the void fraction values with associated signal attenuation levels.

23. The method of claim 15, wherein the RF signal transmitted through the transportation pipe is multiple RF signals at different modulations or frequencies.

24. The method of claim 15, wherein the receiver antenna is adapted to transmit a signal, and wherein the RF signal transmitted through the transportation pipe is transmitted by the receiver antenna.

* * * * *